US00PP12876P2

(12) United States Plant Patent
Meilland

(10) Patent No.: US PP12,876 P2
(45) Date of Patent: Aug. 20, 2002

(54) HYBRID TEA ROSE PLANT NAMED 'MEIBOSNIO'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/706,713

(22) Filed: Nov. 7, 2000

(51) Int. Cl.[7] ..... A01H 5/00
(52) U.S. Cl. ..... Plt./134
(58) Field of Search ..... Plt./134, 130, 145

(56) References Cited

PUBLICATIONS

UPOV–ROM GTITM Computer Database 2001/04, Aug. 6, 2001, GTI Jouve Retieval Software, Citation for Rosa 'Meibosnio'.*
French Breeders Rights Application No. 16729, filed Apr. 19, 1999, 'Meibosnio' Rose.
Protection Des Obtentions Vegetales, Bulletin Officiel du Comité de la Protection des Obtentions Végétales, Cover Pages and pp. 205, 207 and 211 (May 10, 1999).
Protection Des Obtentions Vegetales, Bulletin Officiel du Comité de la Protection des Obtentions Végétales, Cover Page and pp. 342 and 348 (Sep. 10, 1999).

* cited by examiner

*Primary Examiner*—Bruce R. Campell
*Assistant Examiner*—June Hwu
(74) *Attorney, Agent, or Firm*—Burns, Doane, Swecker & Mathis L.L.P.

(57) ABSTRACT

A new and distinct variety of Hybrid Tea rose plant is provided which abundantly forms attractive very double blossoms that are a blend of yellow and salmon pink. The plant exhibits a bushy strong vigorous growth habit, dense dark green foliage, and excellent disease resistance particularly with respect to Black Spot. The attractive dark green foliage contrasts nicely with the light-colored blossoms. The new variety is particularly well suited for growing as attractive ornamentation in the landscape such as in parks and gardens.

1 Drawing Sheet

SUMMARY OF THE INVENTION

Figures 1, 2, 3, 4, 5, 6, 7, 8, 9, 10, 11, 12, 13, 14, 15, 16:
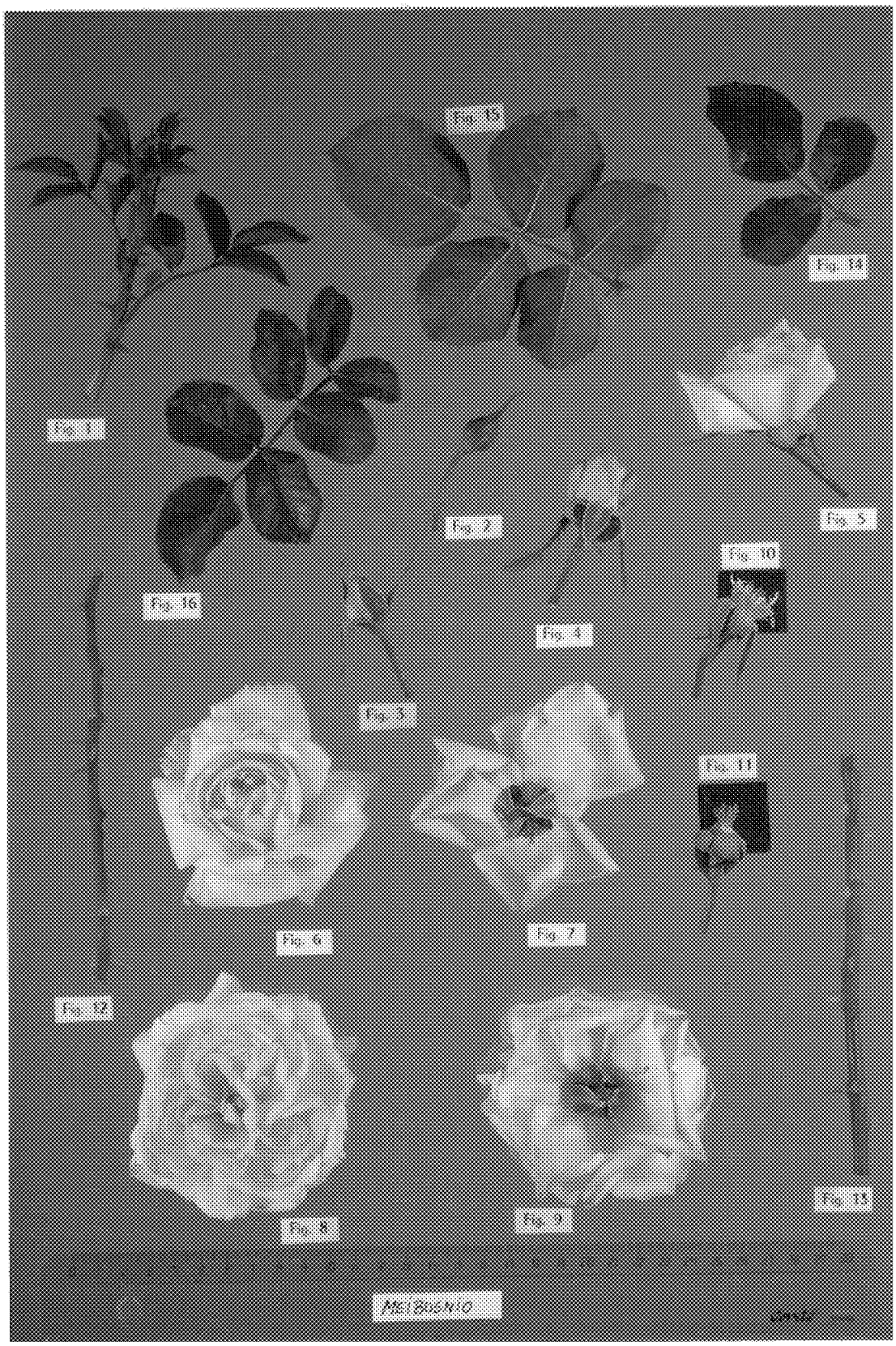

The new variety of *Rosa hybrida* Hybrid Tea rose plant was created by artificial pollination wherein two parents were crossed which previously had been studied in the hope that they would contribute the desired characteristics. The female parent (i.e., the seed parent) of the new variety was the 'Meicloux' variety (non-patented in the United States). The male parent (i.e., the pollen parent) was the product of the cross of the 'Paloma Blanca' variety (U.S. Plant Pat. No. 2,853) and the 'Bucbi' variety (U.S. Plant Pat. No. 4,225). The parentage of the new variety can be summarized as follows:

'Meicloux'×('Paloma Blanca'×'Bucbi').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) exhibits a bushy strong vigorous growth habit,
(b) abundantly forms attractive very double blossoms that are a blend of yellow and salmon pink,
(c) forms dense dark green non-glossy foliage that contrasts well with the light-colored blossoms,
(d) exhibits excellent resistance to Black Spot, and
(e) is particularly well suited for growing as attractive ornamentation in the landscape.

The new variety of the present invention can be readily distinguished from its parental varieties. More specifically, the 'Meicloux' female parent forms blossoms that display an orange blend coloration, the 'Paloma Blanca' variety forms ivory white blossoms in clusters, and the 'Bucbi' variety forms light pink blossoms that possess a pointed configuration.

The new variety well meets the needs of the horticultural industry and can be grown to advantage in parks and gardens.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meibosnio' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing in outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of one year-old plants during October while budded on *Rosa froebelli* understock and growing outdoors at Le Cannet des Maures, Var, France. The coloration in more common terms precedes reference to the chart in some instances. Such terminology is to be accorded its ordinary dictionary significance.

Botanical classification: *Rosa hybrida*, cv. 'Meibosnio'.
Class: Hybrid tea.
Plant:
- *Height.*—Approximately 70 to 90 cm on average at the end of the growing season.
- *Width.*—Approximately 60 to 70 cm on average at the end of the growing season.
- *Habit.*—Bushy.

Branches:
- *Color.*—Young stems: near Yellow-Green Group 146B with some anthocyanin coloration near Greyed-Orange Group 183A. Adult wood: near Yellow-Green Group 146B.
- *Thorns.*—Size: large (as illustrated), and approximately 1 cm in length on average. Quantity: moderately numerous (as illustrated). Color: near Greyed-Orange Group 165B on young stems and near Greyed-Orange Group 163B on adult wood. Configuration: slightly curved at the base on the upper side and slightly concave on the under side.

Leaves:
- *Stipules.*—Adnate, pectinate, and broad.
- *Petioles.*—Upper surface: near Green Group 139A. Under surface: near Green Group 139B.
- *Leaflets.*—Number: 3, 5 (most often), and 7. Shape: elliptic with an obtuse base and a cuspidate tip. Serration: simple and regular (as illustrated). Texture: smooth. General appearance: very dense, dark green, and dull. Color (young foliage): Upper surface: near Yellow-Green Group 146B with anthocyanin coloration near Greyed-Red Group 178B. Under surface: near Yellow-Green Group 146B with anthocyanin coloration near Greyed-Red Group 178B. Color (adult foliage): Upper surface: near Green Group 139A. Under surface: near Yellow-Green Group 146A.

Inflorescence:
- *Number of flowers.*—Usually one to three flowers per stem.
- *Peduncle.*—Yellow-Green Group 146B with some anthocyanin coloration near Greyed-Purple Group 182A, and the length is approximately 5 to 6 cm on average. Some pubescence commonly is present.
- *Sepals.*—Upper surface: tomentose, and near Yellow-Green Group 147B with some anthocyanin coloration near Greyed-Purple Group 182A. Under surface: smooth with glandular edges, near Yellow-Green Group 147A with some anthocyanin coloration and some extensions (as illustrated). Size: commonly approximately 1.2 cm in length on average and approximately 0.5 cm in width on average.
- *Buds.*—Shape: globular. Size: large. Length: approximately 2.5 cm on average. Color upon opening: Upper surface: Yellow-Orange Group 15A, to Yellow-Orange Group 15D. Under surface: Yellow-Orange Group 15A to Yellow-Orange Group 15D and suffused with Orange Group 28B and Orange Group 28C at the margin.
- *Flower.*—Shape: cup-shaped. Diameter: approximately 12 to 13 cm on average. Color (when opening begins): Upper surface: the internal petals are near Yellow-Orange Group 15B and the external petals are near Yellow-Orange Group 15C and Yellow-Orange Group 15D and are suffused with Orange Group 28D at the margin. Under surface: the internal petals are near Yellow-Orange Group 15B and the external petals are near Yellow-Orange Group 15C and Yellow-Orange Group 15D and are suffused with Orange Group 28D at the margin. Color (when blooming): Upper surface: the internal petals are near Yellow-Orange Group 15B and the external petals are near Yellow-Orange Group 15C and Yellow-Orange Group 15D and are suffused with Orange Group 28D at the margin. Under surface: the internal petals are near Yellow-Orange Group 15B and the external petals are near Yellow-Orange Group 15C and Yellow-Orange Group 15D and are suffused with Orange Group 28D at the margin. Color (at end of opening): Upper surface: the internal petals are near Yellow-Orange Group 15C and the external petals are near Yellow-Orange Group 15D suffused with Orange Group 29D at the margin. Under surface: the internal petals are near Yellow-Orange Group 15C and the external petals are near Yellow-Orange Group 15D suffused with Orange Group 29D at the margin. Fragrance: none. Lasting quality: very long on the plant. The blossoms commonly last approximately 10 days on the plant. Since the new variety is primarily intended to provide ornamentation outdoors, the lasting qualities of the blossoms when cut and placed in a vase have not been evaluated. Petal number: approximately 70 to 75 on average. Petal shape: obtuse base with a reflexed tip. Petal size: commonly approximately 4.3 cm in length on average and approximately 4.6 cm in width on average. Petal texture: relatively thin. Petaloids: none observed to date. Stamen number: approximately 48 on average. Anthers: near Yellow-Orange Group 17C in coloration. The size commonly is approximately 0.3 cm on average. Filaments: near Yellow-Orange Group 15A in coloration. The lengths commonly are approximately 0.6 cm on average. Pistils: approximately 43 on average. Stigmas: near Red Group 43B in coloration. Styles: near Yellow Group 4D. The lengths commonly are approximately 0.8 cm on average. Receptacle: commonly near Green Group 143B in coloration, and funnel-shaped in longitudinal section. The size is small to medium. Hips: substantially round and approximately 2 cm in diameter. Seeds: substantially round, commonly approximately 5 seeds per hip, approximately 0.5 cm across, and yellowish in coloration.

Development:

*Vegetation.*—Very vigorous and strong.

*Blooming.*—Very abundant.

*Resistance to diseases.*—Excellent especially with respect to Black Spot, Rust and Powdery Mildew.

*Aptitude to bear fruit.*—Low.

*Hardiness.*—Good above approximately −10° C.

I claim:

1. A new and distinct variety of Hybrid Tea rose plant characterized by the following combination of characteristics:

(a) exhibits a bushy strong vigorous growth habit, (b) abundantly forms attractive very double blossoms that are a blend of yellow and salmon pink, (c) forms dense dark green non-glossy foliage that contrasts well with the light-colored blossoms, (d) exhibits excellent resistance to Black Spot, and (e) is particlarly well suited for growing as attractive ornamentation in the landscape;

substantially as herein shown and described.

* * * * *

McBucklo